United States Patent [19]

Kuhn et al.

[11] Patent Number: 4,960,539

[45] Date of Patent: Oct. 2, 1990

[54] USE OF FLUOROMETHYLPHENOLS AS SOLVENTS FOR LC-POLYMERS, AND NEW FLUOROMETHYLPHENOLS

[75] Inventors: Rainer Kuhn, Odenthal; Albrecht Marhold, Leverkusen; Hans-Rudolf Dicke, Krefeld, all of Fed. Rep. of Germany

[73] Assignee: Bayer Aktiengesellschaft, Leverkusen, Fed. Rep. of Germany

[21] Appl. No.: 431,677

[22] Filed: Nov. 2, 1989

Related U.S. Application Data

[63] Continuation of Ser. No. 174,654, Mar. 29, 1988, abandoned.

[30] Foreign Application Priority Data

Apr. 15, 1987 [DE] Fed. Rep. of Germany ....... 3712817

[51] Int. Cl.$^5$ .............................................. C09K 19/52
[52] U.S. Cl. ................................. 252/299.5; 252/364; 252/299.01
[58] Field of Search ................ 252/364, 299.01, 299.5; 428/1

[56] References Cited

U.S. PATENT DOCUMENTS

| | | | |
|---|---|---|---|
| 4,157,344 | 6/1979 | Feiring | 260/575 |
| 4,225,731 | 9/1980 | Marhold et al. | 568/775 |
| 4,624,872 | 11/1986 | Stuetz | 428/1 |

FOREIGN PATENT DOCUMENTS

286953A 10/1988 European Pat. Off. ......... 252/299.5

OTHER PUBLICATIONS

*Chemical Abstracts,* 28, 3956n, vol. 78, 1973.
Patent Abstracts of Japan, Band 11, Nr. 18 (C–398) (2465), 1/17/87.

*Primary Examiner*—John S. Maples
*Assistant Examiner*—Richard Treanor
*Attorney, Agent, or Firm*—Sprung Horn Kramer & Woods

[57] ABSTRACT

Certain fluoromethylphenols, such as 3,5-bis-trifluoromethylphenol, are suitable solvents for LC-polymers. Many LC-polymers which have hitherto been regarded as insoluble in organic solvents can be brought into solution by means of these compounds. The polymers thereby become more easily analyzable and can be processed from solution.

12 Claims, No Drawings

USE OF FLUOROMETHYLPHENOLS AS SOLVENTS FOR LC-POLYMERS, AND NEW FLUOROMETHYLPHENOLS

This application is a continuation of application Ser. No. 174,656, filed 3/29/99, now abandoned.

This invention relates to the use of certain fluoromethylphenols as solvents for so called LC (liquid-crystalline)polymers. The invention also relates to some new fluoromethylphenols suitable for this purpose.

By virtue of their exceptional properties, LC-polymers, especially LC-polyesters, are becoming increasingly important in the fields of thermoplastic constructional materials, high strength fibres and filaments and heat resistant coatings. In practice, difficulties in handling these LC-polymers frequently occur because some of these high molecular weight compounds are insoluble in the usual organic solvents under normal conditions while others, although initially soluble in these organic solvents, become sparingly soluble or even completely insoluble as a result of an after condensation which is carried out to increase the molecular weight for the purpose of improving the mechanical properties.

Pentafluorophenol is sometimes recommended as a special solvent for difficultly soluble LC-Polymers (R. W. Lenz, "Synthetic Routes to Liquid Crystalline Polymers" in "Recent Advances in Liquid Crystalline Polymers", Elsevier, New York 1985), but even this solvent fails in many cases.

It has now surprisingly been found that certain trifluoromethylphonols are superior to pentafluorophenol in their power to dissolve difficultly soluble LC-polymers.

The present invention therefore relates to the use of compounds corresponding to the following formula

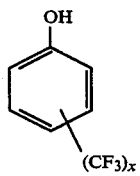
(I)

wherein x represents an integer with a value of from 1 to 5, preferably 2 or 3,
as solvents for LC-polymers,
which compounds (1) may in addition contain up to (5-x) substituents selected from
(1) $C_1$ to $C_4$ alkyl,
(2) Halogen-selected from fluorine and chlorine,
(3) Mono- or poly-fluoro-$C_1$ to $C_4$ alkyl (preferably mono- or di-fluoromethyl) which may be substituted by hydrogen, chlorine or bromine atoms, and
(4) $C_1$ to $C_4$ alkyl optionally substituted by fluorine or chlorine.

Compounds (I) containing substituents from category (3) are preferred.

Examples of preferred compounds (I) include phenols and cresols containing from 1 to 3 $CF_3$ substituents, phenols containing 1 or 2 $CF_3$ substituents and 3 or 4 halogen atoms, phenols containing 1 or 2 $CF_3$ substituents and 1 or 2 $C_1$ to $C_4$ alkoxy groups, phenols containing 1 or 2 $CF_3$ substituents and 1 or 2 $CHF_2$ or $CF_2Cl$ groups and phenols containing 1 or 2 $CF_3$ substituents and 1 or 2 $OCF_3$ groups.

The following are examples of particularly preferred compounds (I):
(a) m-trifluoromethylphenol,
(b) p-trifluoromethylphenol,
(c) 2-chloro-4-trifluoromethylphenol,
(d) 2,6-dichloro-4-trifluoromethylphenol,
(e) 2-isopropyl-5-trifluoromethylphenol,
(f) 2,4,6-tribromo-5-trifluoromethylphenol,
(g) 2-chloro-3,4,5-trifluoro-6-trifluoromethylphenol,
(h) 2-chloro-3,5,6-trifluoro-4-trifluoromethylphenol,
(i) 2,3,5,6-tetrafluoro-4-trifluoromethylphenol,
(k) 3-trifluoromethyl-4-trifluoromethoxyphenol,
(l) 3-trifluoromethyl-4-difluorochloromethoxyphenol,
(m) 2,4,5-tris-trifluoromethylphenol, and especially
(n) 3,5-bis-trifluoromethylphenol.

Compounds (I) and processes for their preparation are generally known; see, for example, FR 1 469 596, SU 520 343, DE 2 016 624, US 2 489 423, 2 547 679; J. Res. Nat. Bur. Std. 67 A (5), 481–493 (1963), Chem. Abstr. 60, 9170 c (1964), Jzv. Sib. Obd. Akad. Nauk. SSR, Ges. Khim. Nauk (5), 94–102 (1982), Bull. Acad. Roy. Belg. 1913, 241; J. Org. Chem. 16, 586 (1951), J. Amer. Chem. Soc 71, 4148 (1949), 69. 947 (1947), 73, 3470 (1951).

As a general rule, the corresponding anilines are diazotised and heated to produce the phenol or the corresponding chlorobenzenes are reacted with an alkali, metal hydroxide at an elevated temperature with liberation of hydrogen chloride to form the required phenol.

Some of the compounds (I) which are suitable as solvents are new. The invention therefore also relates to trifluoromethylphenols corresponding to the following formula:

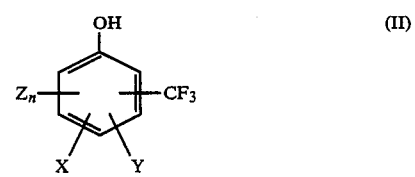
(II)

wherein
X denotes fluoro-$C_1$ to $C_4$-alkyl or fluoro-$C_1$ to $C_4$-alkoxy,
Y denotes fluoro, chloro, fluoro-$C_1$ to $C_4$-alkyl or fluoro-$C_1$ to $C_4$-alkoxy,
Z denotes fluorine or chlorine and
n has the value 0, 1 or 2,
with the proviso that n has the value 1 or 2 when $X=Y=CF_3$.

Preferred compounds (II) correspond to the above formula in which either X denotes $OCF_3$, $OCF_2Cl$ and Y denotes hydrogen or X and Y both stand for $CF_3$ and n stands for 0.

Preferred compounds (II) include, for example, 2,4,5-tristrifluoromethylphenol, 3-trifluoromethyl-4-trifluoromethoxyphenol and 3-trifluoromethyl-4-difluorochloromethoxyphenol.

The new compounds may be prepared by processes analogous to those used for the preparation of the known compounds (I), e.g. by diazotisation followed by boiling of the corresponding anilines or by reaction of the corresponding halobenzenes with alkalimetal hydroxides at elevated temperatures.

LC-polymers are well known; see, for example, F. E. McFarlane et. al., Liquid Crystal Polymers II. Contemporary Topics in Polymer Science, Vol. 2, Plenum Publishing Corporation, 1977;

W. J. Jackson and H. F. Kuhfuss, J. Polymer Science, Polymer Chem. Ed. 14, 2042 (1976);

W. C. Wooten et. al. in "Ultra-high Modulus Polymers" by A. Ciferri, Applied Science Publ., London 1979, page 362 et seq;

A. Blumstein et. al., "Liquid Crystalline Order in Polymers", Academic Press 1978;

J. Preston, Angew. Makromol. Chem. 109/110, pages 1-19 (1982);

A. Cifferri, W. R. Krigbaum, R. B. Meyer "Polymer Liquid Crystals", Academic Press, New York, 1982;

P. J. Flory, I. Uematsu, S. P. Papkov, C. H. Ober and R. W. Lenz, Advances in Polymer Science 59 (1984):

B. Wunderlich, J. Grebowicz, M. G. Dobb, J. McIntyre, H. Finkelmann, G. Rehage, V. P. Shibaev and N. Plate, Advances in Polymer Science 60/61 (1984);

EP 1185, 1340, 8855, 11 640, 15 856, 17 310, 18 145, 18 709, 22 344, 44 205, 49 615;

US 3 991 013, 3 991 014, 4 066 620, 4 067 852, 4 083 829, 4 107 143;

US 3 991 013, 3 991 014, 4 066 620, 4 067 852, 4 083 829, 4 107 143;

WO 79/797, 79/1034, 79/1040.

The liquid-crystalline state of polymer melts may be investigated by means of a polarisation microscope. For these investigations, the eye piece is fitted with an attachment containing a photoelectric diode at the focal point of the ocular lens. A measuring amplifier with control device is attached for adjusting the measuring value in the absence of a sample to 100 scale units while the microscope is switched on and Nicol prisms are arranged in parallel. When the Nicol prisms are crossed, a value of 0.01 scale units is then obtained.

The layer thickness of the polymer melts investigated is 100 μm.

Examination of the polymers is carried out at 200° to 400° C. after the samples have been melted. If over this whole range or a Part thereof the melt is seen to brighten between the crossed Nicol prisms, the polymer is classified as liquid-crystalline.

In the measuring arrangement, the liquid-crystalline polymers show values above 1 scale unit, in most cases from 3 to 90 scale units. For amorphous melts, e.g. aromatic polycarbonates, values of less than 0.1 scale division are obtained.

The method of thermo-optical testing (TOT) described above is particularly suitable for rapid determination in the laboratory and gives unequivocal results in almost all cases.

In cases of doubt, it may be advisable to confirm the presence of liquid-crystalline components by means of X-ray scattering in the melt as described, for example, by G. W. Gray and P. A. Windsor in "Plastic Crystals, Physico-Chemical properties and Methods of Investigation", in particular chapter 3, John Wiley & Sons, New York, Sydney, Toronto, 1974.

The following are examples of suitable LC-polymers: polyesters, polythiol esters, polyester amides, polyester imides, polyazomethines and polyestercarbonates.

Preferred LC-polymers are fully aromatic polyesters based on
(a) aromatic dicarboxylic acids
(b) diphenols and optionally
(c) aromatic hydroxycarboxylic acids, in which the molar ratio of moieties of aromatic dicarboxylic acids incorporated by condensation to moieties of diphenols incorporated by condensation is from 0.95 to 1.05 and the moieties of aromatic hydroxycarboxylic acids incorporated by condensation amount to from 0 to 100 mol %, preferably from 30 to 80 mol %, in particular from 50 to 70 mol %, based on the condensed moieties (a) and (c).

Aromatic dicarboxylic acids (a) include all those dicarboxylic acids in which the carboxyl groups are directly attached to an aromatic ring.

Preferred aromatic dicarboxylic acids (a) correspond to the formula

HOOC—A—COOH       (III)

wherein
A denotes a bivalent aromatic group having from 6 to 24 carbon atoms, preferably from 6 to 16 carbon atoms.

Preferred aromatic groups A are those in which the two bonds to the carboxyl groups extend coaxially in opposite directions, as for example in 1,4-phenylene, 1,4-napthylene or 4,4'-biphenylene, or in which the bonds extending in opposite directions are shifted parallel to one another, as for example in 1,5-naphthylene, 2,6-naphthylene or 3,5'-biphenylene.

Aromatic groups A in which the two bonds to the carboxyl groups do not extend in opposite directions either coaxially or with parallel displacement are also suitable, provided the two bonds enclose an angle of from 45° to less than 180° and are not attached to immediately adjacent carbon atoms, for example as in 1,3-phenylene, 1,3-, 1,6-, 1,7- or 2,7-naphthylene or 3,4'-biphenylene.

Examples of preferred aromatic dicarboxylic acids (a) include 1,4-naphthalene dicarboxylic acid,1,5-naphthalene dicarboxylic acid, 2,6-naphthalene dicarboxylic acid, 4,4'-biphenyl-dicarboxylic acid, 3,3'-biphenyl-dicarboxylic acid, 4,4'-diphenoxyethane-dicarboxylic acid, 4,4'-diphenyletherdicarboxylic acid, methyl-terephthalic acid, methoxyterephthalic acid, chloroterephthalic acid, 4-chloronaphthalene-2,7-dicarboxylic acid, 1,3-naphthalene-dicarboxylic acid, 1,6-naphthalene-dicarboxylic acid, 1,7-naphthalene-dicarboxylic acid, 2,7-naphthalene-dicarboxylic acid, 3,4'-biphenyl-dicarboxylic acid, 3,4'-diphenylether-dicarboxylic acid, 4-methyl-isophthalic acid, 5-methyl-isophthalic acid, 4,4-dichloro-diphenylether-3,3'-dicarboxylic acid, 4,4'-benzophenone-dicarboxylic acid and 3,4'-benzophenone-dicarboxylic acid. Iso- and terephthalic acid are particularly preferred aromatic dicarboxylic acids (a).

Preferred diphenols (b) correspond to the following formula:

HO—D—OH       (IV)

wherein
D denotes a divalent mononuclear or polynuclear aromatic group having from 6 to 30 carbon atoms and is so constructed that each of the two OH groups are directly attached to a carbon atom of an aromatic system and the two bonds to the Phenolic hydroxyl groups enclose an angle of from 45° to 180°. As for the constitution, the same applies to the group D as has been described above for the aromatic group A.

The following are examples of particularly preferred diphenols (b): hydroquinone, 4,4'-dihydroxy-diphenyl, 4,4'-dihydroxydiphenylether, 4,4'-dihydroxy-diphenylethane, 4,4'-dihydroxydiphenoxyethane, 3,5'-dihydroxy-diphenyl, 3,5'-dihydroxydiphenylether, 1,5-dihydroxy-naphthalene, 2,6-dihydroxynaphthalene, 1,4-dihydroxy-naphthalene, chlorohydroquinone, bromohydroquinone, methylhydroquinone, phenylhydroquinone, ethylhydroquinone, 2,2'-dimethyl-4,4'-dihydroxy-diphenyl, 3,3',5,5'-tetramethyl-4,4'-dihydroxy-diphenyl, 3,5'-dimethoxy-4,4'-dihydroxy-diphenylether, 1,2-(2-chloro-4-hydroxyphenoxy)ethane, 4-methoxy-2,6-dihydroxy-naphthalene, resorcinol, 3,4'-dihydroxy-diphenyl, 3,4'-dihydroxy-diphenylether, 3,4'-dihydroxy-diphenoxyethane, 1,3-dihydroxy-naphthalene, 1,6-dihydroxy-naphthalene, 1,7-dihydroxy-naphthalene, 2,7-4-methylresorcinol, 4-phenylresorcinol, 4-ethoxyresorcinol, 2,5-dichloro-1,6-dihydroxy-naphthalene and 4-methoxy-2,7-dihydroxy-naphthalene.

Hydroquinone, resorcinol and 4,4'-dihydroxy-diphenyl are particularly preferred diphenols (b).

Compounds corresponding to the following formulae are examples of preferred aromatic hydroxycarboxylic acids (c):

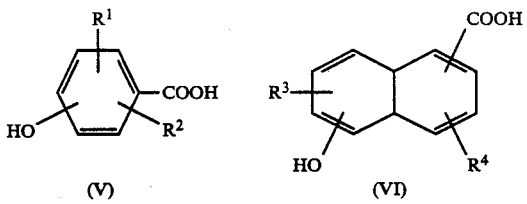

in which formulae,
Rhu 1 to $R^4$ denotes $C_1$ to $C_4$ alkyl, $C_1$ to $C_4$ alkoxy, $C_6$ to $C_{10}$ aryl or aryloxy, $C_7$ to $C_{12}$ aralkyl (preferably benzyl), halogen (preferably chlorine and bromine) or hydrogen and the bonds between the nucleus and the hydroxyl group or carboxyl group enclose an angle of from 45° to 180°.

The following are examples of particularly preferred aromatic hydroxycarboxylic acids (c): 4-hydroxy-3-methyl-benzoic acid, 4-hydroxy-3-phenyl-benzoic acid, 4-hydroxy-2-ethyl-benzoic acid, 3-chloro-4-hydroxy-benzoic acid, 3-bromo-4-hydroxybenzoic acid, 4-hydroxy-3-methoxy-benzoic acid, 4-methyl-3-hydroxy-benzoic acid, 4-hydroxy-3-phenoxy-benzoic acid, 6-hydroxy-5-chloro-2-naphthoic acid, 6-hydroxy-5-methyl-2naphthoic acid, 6-hydroxy-5-methoxy-2-naphthoic acid, and 6-hydroxy-4,7-dichloro-2-naphthoic acid.

Unsubstituted hydroxycarboxylic acids such as p-hydroxybenzoic acid and 6-hydroxy-2-naphthoic acid are particularly preferred aromatic hydroxycarboxylic acids (c).

Not all combinations of the starting materials listed above give rise to LC-polyesters. The man of the art will choose suitable combinations on the basis of the literature references given above or of his own experience.

As end groups, the LC-polyesters may contain COOH, H, OH, $OC_6H_5$, acyloxy or residues derived from chain breaking agents. Preferred chain breaking agents include monofunctional aromatic hydroxyl compounds such as 4-hydroxydiphenyl, p-nonylphenol, 4-(1,1,3,3-tetramethylbutyl)phenol or β-naphthol; and aromatic monocarboxylic acids such as diphenylcarboxylic acids and naphthalene carboxylic acids. End groups may be present in quantities of from 0.5 to 5 mol %, based on the sum of aromatic dicarboxylic acid groups (a) and diphenol groups (b) present.

The LC-polyesters may be branched by means of trifunctional or higher functional, preferably aromatic monomers. The quantity of branching compounds is generally from 0.1 to 1 mol %, based on the sum of aromatic dicarboxylic acid residues (a) and diphenol residues (b). Examples of preferred branching agents include phloroglucinol, 1,3,5-benzene-tricarboxylic acid and 3,5-dihydroxy-benzoic acid.

The LC-polyesters generally have an inherent viscosity of at least 0.5, preferably at least 1.0 dl/g (determined on a solution of 5 mg of polyester per ml of p-chlorophenol at 45° C). If the polyesters are insoluble in p-chlorophenol, it is assumed that they have the required minimum viscosity.

The preferred LC-polymers also include fully aromatic LC-polyester carbonates, i.e. fully aromatic polyesters, for example as described above, in which the aromatic dicarboxylic acid groups are partially replaced by carbonyl groups, preferably to an extent of from 60 to 100 mol %, in particular from 60 to 90 mol %.

Preferred fully aromatic LC-polyester carbonates B include polycondensates based on
(a) (optionally substituted) p-hydroxybenzoic acid,
(b) diphenol,
(c) carbonic acid, optionally
(d) aromatic dicarboxylic acid and optionally
(e) chain breaking agents,
in which a proportion of the diphenol groups (b) is present as 4,4'-dihydroxy-biphenyl groups (f) and the following molar ratios apply to the groups, apart from the end groups:
a+b=1,
b=c+d,
f=0.1 to 0.9, preferably 0.11 to 0.7, in particular 0.125 to 0.4, and $$\frac{c}{c+d} = 0.6 \text{ to } 1, \text{ preferably } 0.6 \text{ to } 0.9;$$

a=0.4 to 0.8, preferably 0.6 to 0.75,
b-f=02 to 0.053, preferably 0.06 to 0.36, in particular 0.1 to 0.35,
c=0.12 to 0.6, preferably 0.175 to 0.4,
d=0 to 0.24, preferably 0 to 0.12 and
f=0.02 to 0.53, preferably 0.0275 to 0.28, in particular 0.3 to 0.16.

Compounds corresponding to the formulae (V) and (VI) are preferred (a) p-hydroxybenzoic acids.

Compounds corresponding to formula (IV) are preferred (b) diphenols.

Compounds corresponding to formula (III) are preferred (d) aromatic dicarboxylic acids.

The fully aromatic LC-Polyester carbonates may, for example, contain the end groups mentioned in connection with the fully aromatic LC-polyesters.

The fully aromatic LC-polyester carbonates may contain the units (a) to (d) and (f) in random distribution or in blocks.

The fully aromatic LC-polyester carbonates generally have an inherent viscosity of at least 0.5, preferably at least 1.0 dl/g (determined on a solution of 5 mg of polyester carbonate per ml of p-chlorophenol at 50° C.).

The LC-polymers may be subjected to a solid phase after condensation to improve their properties. This is generally carried out for 1 to 25 hours at from 200° to 300° C. and at reduced pressure.

Although the compounds (I) which are to be used as solvents are, of course, capable of dissolving those LC-polymers which have not hitherto been difficult to dissolve, it . would appear to be most valuable to use the compounds (I) for dissolving those LC-polymers which have hitherto been regarded as insoluble.

In the present context, an LC-polymer is described as "insoluble" if a sample of 0.1 g of the LC-polymer dissolves to an extent of less than 90% by weight in 1 ml of pentafluorophenol in the course of 24 hours at 100° C.

The LC-polymers in many cases dissolve slowly in compounds (I) but the process of solution may be accelerated by raising the temperature of the solvent and/or size reducing the LC-polymer. It is generally sufficient to shake or stir the sample at room temperature for some hours or, in the case of high concentrations, for up to several weeks but the process may be accelerated by heating the solvent to temperatures of up to 120° C. or higher.

The solutions obtained may have concentrations of from 0.01 to 30% by weight, preferably from 0.1 to 10% by weight, depending on the molecular weight and chain rigidity of the LC-polymer.

The compounds (I) will dissolve not only LC-Polymers but also numerous other hi8h molecular weight compounds, e.g. polyesters such as polyethyleneterephthalate and polybutyleneterephthalate, polyamides, polycarbonates, styrene/acrylonitrile copolymers and polystyrene.

By dissolving the LC-polymers, the compounds (I) enable LC-polymers to be spun by solution spinning, which has hitherto been impossible owing to the insolubility of the LC-polymers. Since, as stated above, the compounds (I) are capable of dissolving not only LC-polymers but also numerous other polymers, the compounds (I) may also be used as solvents to prepare mixed fibres.

The solutions of LC-polymers may be used as high temperature resistant and solvent resistant coating and impregnating agents for coating and impregnating a wide variety of substrates such as metal, wood and textile fibres. The solutions may also be used for the preparation of cast films. When polymer mixtures containing at least one polymer which is soluble in another solvent and at least one polymer which is insoluble in this solvent are dissolved in compounds (I) and the resulting solutions are cast to form films, the products obtained may serve as high temperature resistant and solvent resistant membranes.

Furthermore, the compounds (I) also enable LC-polymers which have hitherto been regarded as insoluble to be investigated analytically. Thus, for example, the solutions obtained may be used for viscosity measurements, static and dynamic light scattering measurement, gel permeation chromatography, precipitation and solution fractionation, osmometric measurements and NMR spectroscopy.

The percentages mentioned in the following examples are based on weight.

EXAMPLES

1. Preparation of new fluoromethylphenols (a) Preparation of 4-trifluoromethoxy-3-trifluoromethylphenol.

50 g of 4-trifluoromethoxy-3-trifluoromethylaniline are diazotised in 400 ml of acetic acid and 50 ml of sulphuric acid by the drop-wise addition of 74 g of a 40% nitrosyl sulphuric acid at 5° C. The mixture is then stirred for 1 hour at 20° C. The resulting diazonium salt solution is added drop-wise to a mixture, heated to 100° C., of 400 ml of 50% sulphuric acid, 20 g of copper sulphate and 2 g of copper oxide. When all the diazonium salt solution has been added, the phenol is driven off with steam, extracted with dichloromethane in the receiver and distilled. 38 g of product are obtained (B.pt: 80°–3° C./20 mbar, $n_D^{20}$:1.4218).

(b) 4-difluorochloromethoxy-3-trifluoromethylphenol (B pt: 105–8° C./20 mbar, $n_D^{20}$:1.4455) is obtained in analogous manner from 4-difluorochloromethoxy-3-trifluoromethylaniline.

(c) Preparation of 2-4,5-tris-trifluoromethylphenol 50 g of tertiary butanol, 30 g of 2,4,5-tris-tri-fluoromethylchlorobenzene and 12 g of sodium hydroxide are dissolved successively in 75 ml of DMSO and then heated under reflux for 8 hours. After cooling, the reaction mixture is poured into 250 ml of water and acidified with hydrochloric acid, the product is extracted with toluene, and the solution in toluene is washed with water and dried. 18 g of product are obtained by distillation (B.pt: 121°–124° C./20 mbar).

2. Preparation of 3,5-bis-trifluoromethylphenol

Carried out according to US-PS 2 547 679, column 4, lines 12 to 25.

3. Solubility of LC-polymers (a) The following polymers were used:

I Fully aromatic polyester of 31.2 mol of p-hydroxybenzoic acid, 14.4 mol of isophthalic acid, 2.4 mol of terephthalic acid, 14.4 mol of hydroquinone and 2.4 mol of 4,4'-dihydroxydiphenyl having a melt viscosity (determined at 330° C. and a shearing velocity of $10^3$ sec$^{-1}$) of 280 Pa.s.

II Fully aromatic polyester carbonate containing 68 parts by weight of residues of p-hydroxybenzoic acid, 28 parts by weight of hydroquinone residues, 29 parts by weight of carbonate structures, 4 parts by weight of residues of 4,4'-dihydroxy-diphenyl and 2.7 parts by weight of terephthalic acid residues and having a melt viscosity (determined at 330° C. and a shearing velocity of $10^3$ sec$^{-1}$) of 100 Pa s.

III ®Vectra B 900 (trade product of Celanese), a fully aromatic polyesteramide of 2-hydroxynaphthoic acid, p-aminophenol and terephthalic acid, melting point about 290° C.

IV ®Xydar SRT 300 (trade product of Dartco), a fully aromatic polyester of p-hydroxybenzoic acid, terephthalic acid and 4,4'-dihydroxydiphenyl, having a melting point of about 420° C.

| | Solution Conditions | | | Solvent | | |
|---|---|---|---|---|---|---|
| Product | Concentration (g/ml) | Temperature* (°C.) | Time (hours) | Pentafluorophenol | 3,5-bis-trifluoromethyl-phenol (BTFMP) | Limiting Viscosity (dl/g) in BTFMP at 120° C. |
| I | 0.01 | 50; 25 | 12 | — | + | 2.37 |

-continued

| | Solution Conditions | | | Solvent | | Limiting Viscosity (dl/g) in BTFMP at 120° C. |
|---|---|---|---|---|---|---|
| Product | Concentration (g/ml) | Temperature* (°C.) | Time (hours) | Pentafluorophenol | 3,5-bis-trifluoromethylphenol (BTFMP) | |
| II | 0.01 | 50; 25 | 24 | — | + | 3.60 |
| III | 0.01 | 50; 25 | 48 | — | + | 4.10 |
| IV | 0.01 | 50; 25 | 48 | — | + | 8.90 |

*in pentafluorophenol; in 3,5-bis-trifluoromethylphenol

4. Application

A solution of ®Vectra B 900 in 3,5-bis-trifluoromethylphenol (1% by weight) was cast on a glass plate. The solvent was evaporated off at 160° C. within 1 minute and the film obtained was pulled off by means of tweezers (thickness about 1 μm). The film obtained was free from blisters and found to be optically homogeneous when viewed by the naked eye.

What is claimed is:

1. A composition comprising a solution of a liquid-crystalline polymer, said liquid-crystalline polymer selected from the group consisting of polyesters, polythiol esters, polyester amides, polyester imides, polyazonethines and polyester carbonates, and a solvent, said solvent being a compound of the formula

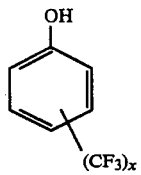

wherein
x represents an integer of from 1 to 5 and said compound comprising either no further ring substituents other than hydrogen or being substituted by 1 to 4 substituents selected from the group consisting of $C_1$-$C_4$ alkyl, fluorine, chlorine, fluoro-$C_1$-$C_4$ alkyl, chloro substituted fluoro-$C_1$-$C_4$-alkyl, bromo substituted fluoro-$C_1$-$C_4$-alkyl, $C_1$-$C_4$ alkoxy, fluoro substituted $C_1$-$C_4$ alkoxy and chloro substituted $C_1$-$C_4$ alkoxy.

2. A composition of claim 1, wherein the formula X represents 2 or 3.

3. A composition of claim 1, wherein 3,5-bis-trifluoromethylphenol is used as the solvent.

4. A composition according to claim 1, wherein in the formula there are three or four chlorine or fluorine ring substituents.

5. A composition according to claim 1, wherein in the formula there are one or two $C_1$-$C_4$ alkoxy group substituents.

6. A composition according to claim 1, wherein in the formula there are one or two $CHF_2$ or $CF_2Cl$ group substituents.

7. A composition according to claim 1, wherein in the formula there are one or two $OCF_3$ group substituents.

8. A composition according to claim 1, wherein the formula contains one or two $CF_3$ substituents and one or two $C_1$-$C_4$ alkoxy groups.

9. A composition according to claim 1, wherein the formula Contains x being one or two and one or two $CHF_2$ group substituents or $CF_2Cl$ group substituents.

10. A composition according to claim 1, wherein the formula contains x being one or two and one or two $OCF_3$ group substituents.

11. A composition according to claim 1, wherein the compound is selected from the group consisting of
 (a) m-trifluoromethylphenol,
 (b) p-trifluoromethylphenol,
 (c) 2-chloro-4-trifluoromethylphenol,
 (d) 2,6-dichloro-4-trifluoromethylphenol,
 (e) 2-isopropyl-5-trifluoromethylphenol,
 (f) 2,4,6-tribromo-5-trifluoromethylphenol,
 (g) 2-chloro-3,4,5-trifluoro-6-trifluoromethylphenol,
 (h) 2-chloro-3,5,6-trifluoro-4-trifluoromethylphenol,
 (i) 2,3,5,6-tetrafluoro-4-trifluoromethylphenol,
 (k) 3-trifluoromethyl-4-trifluoromethoxyphenol,
 (l) 3-trifluoromethyl-4-difluorochloromethoxyphenol,
 (m) 2,4,5-tris-trifluoromethylphenol and
 (n) 3,5-bis-trifluoromethylphenol.

12. A composition comprising a liquid-crystalline polymer and a solvent, said solvent being a compound of the formula

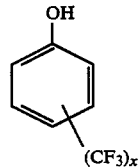

wherein
x represents a integer of from 1 to 5 and said compound comprising either no further ring substituents other than hydrogen or being substituted by 1 to 4 substituents selected from the group consisting of $C_1$-$C_4$ alkyl, fluorine, chlorine, fluoro-$C_1$-$C_4$-alkyl, chloro substituted fluoro-$C_1$-$C_4$-alkyl, bromo substituted fluoro-$C_1$-$C_4$-alkyl, $C_1$-$C_4$ alkoxy, fluoro substituted $C_1$-$C_4$ alkoxy and chloro substituted $C_1$-$C_4$ alkoxy and wherein the liquid crystalline polymer is a fully aromatic polyester based on (a) aromatic dicarboxylic acids and (b) diphenols, with or without (c) aromatic hydroxycarboxylic acids, wherein the molar ration of moieties of aromatic dicarboxylic acids incorporated by condensation to moieties of diphenols incorporated by condensation is from 0.95 to 1.05 and the moieties of aromatic hydrocarboxylic acids incorporated by condensation amount of 0 to 100 mole %, based on the condensed moieties (a) and (c).

* * * * *